(12) United States Patent
Amino et al.

(10) Patent No.: US 7,534,898 B2
(45) Date of Patent: *May 19, 2009

(54) PROCESS FOR PRODUCING MONATIN OR SALT THEREOF

(75) Inventors: Yusuke Amino, Kawasaki (JP); Kazuko Hirasawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 39 days.

This patent is subject to a terminal disclaimer.

(21) Appl. No.: 11/627,700

(22) Filed: Jan. 26, 2007

(65) Prior Publication Data

US 2007/0191464 A1  Aug. 16, 2007

Related U.S. Application Data

(63) Continuation of application No. PCT/JP2005/013993, filed on Jul. 25, 2005.

(30) Foreign Application Priority Data

Jul. 27, 2004   (JP) ............................. 2004-218442

(51) Int. Cl.
 *C07D 209/20* (2006.01)
(52) U.S. Cl. ..................................................... 548/495
(58) Field of Classification Search ................. 548/495
 See application file for complete search history.

(56) References Cited

U.S. PATENT DOCUMENTS

| 2005/0020508 A1 | 1/2005 | Amino et al. |
| 2005/0137246 A1 | 6/2005 | Amino et al. |
| 2005/0272939 A1 | 12/2005 | Amino et al. |

OTHER PUBLICATIONS

March, J. Advanced Organic Chemistry, 4th Edition, p. 896-7.*
U.S. Appl. No. 11/627,700, filed Jan. 26, 2007, Amino, et al.
U.S. Appl. No. 11/505,997, filed Aug. 18, 2006, Mori, et al.
Shigeki Yamada, et al., "Method for the Racemization of Optically Active Amino Acids," J. Org., Chem., 48, 1983, pp. 843-846.

* cited by examiner

*Primary Examiner*—Kamal A Saeed
*Assistant Examiner*—Jason Nolan
(74) *Attorney, Agent, or Firm*—Oblon, Spivak, McClelland, Maier & Neustadt, P.C.

(57) ABSTRACT

To provide a process for producing monatin where steric configuration of 2-position is in an R configuration or a salt thereof by isomerization of 2-position of monatin where steric configuration of 2-position is in an S configuration.

A process for producing monatin where steric configuration of 2-position is in an R configuration or a salt thereof, characterized in that, the process contains a step where isomerization reaction of 2-position of monatin in which steric configuration of 2-position is in an S configuration is carried out in a mixed solvent of water and organic solvent in the presence of an aldehyde and, after that, a step where monatin in which steric configuration of 2-position is in an R configuration or a salt is crystallized.

20 Claims, No Drawings

PROCESS FOR PRODUCING MONATIN OR SALT THEREOF

CROSS-REFERENCE TO RELATED APPLICATIONS

The present application is a continuation of PCT/JP05/13993, filed on Jul. 25, 2005, and claims priority to JP 2004-218442, filed on Jul. 27, 2004.

TECHNICAL FIELD

The present invention relates to a process for producing monatin which is useful as a sweetener and, more particularly, it relates to a process for efficiently producing an optically active monatin where steric configuration at 2-position is in an R configuration.

BACKGROUND ART

It has been known that a (2S,4S) substance of 4-hydroxy-4-(3-indolylmethyl)-2-aminoglutaric acid (hereinafter, it will be sometimes called "monatin") represented by the following formula (3) is contained in bark of root of *Schlerochitom ilicifolius* which is a plant naturally grown in the Northern Transvaal of South Africa, has a sweet taste which is several hundred times as sweet as sucrose and is an amino acid derivative useful as a sweetener (refer to Patent Document 1: Japanese Patent Laid-Open No. 64/025,757).

(3)

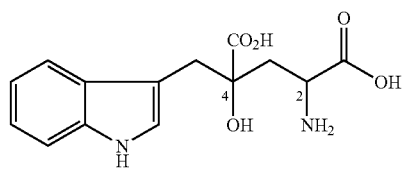

Monatin has asymmetric carbonatoms at 2- and 4-positions and has the following four optical isomers.

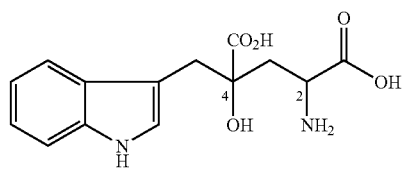

(2S, 4R) Monatin

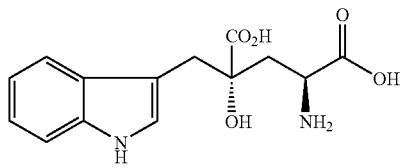

(2R, 4R) Monatin

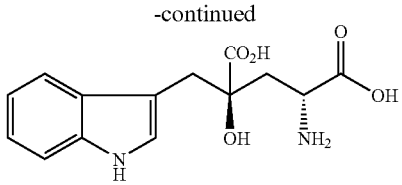

(2R, 4S) Monatin

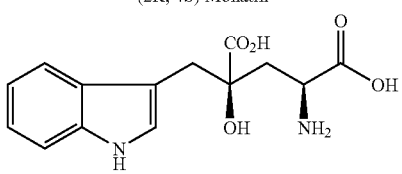

(2S, 4S) Monatin

With regard to a process for producing monatin, there have been many reports (refer to Non-Patent Document 1: *Tetrahedron Letters*, 2001, Vol. 42, No. 39, pages 6793 to 6796; Non-Patent Document 2: *Organic Letters*, 2000, Vol. 2, No. 19, pages 2967 to 2970; Non-Patent Document 3: *Synthetic Communication*, 1994, Vol. 24, No. 22, pages 3197 to 3211; Patent Document 2: U.S. Pat. No. 5,994,559; Patent Document 3: Japanese Patent Laid-Open No. 2002/060,382; etc.) and, although there are examples where several processes for producing optically active monatin are investigated, they need very many steps for the production and are not able to be said to be industrially suitable processes for production.

On the other hand, the present applicant has recently found and reported for a process in which a monatin precursor is synthesized from indole-3-pyruvic acid and, via steps where a diastereomer salt with a specific optically active amine is formed followed by subjecting to an optical resolution, a specific optically active monatin is finally produced (refer to Patent Document 4: WO 03/059,865) When (2R,4R) monatin is taken as an example, the process is able to be represented by the following scheme.

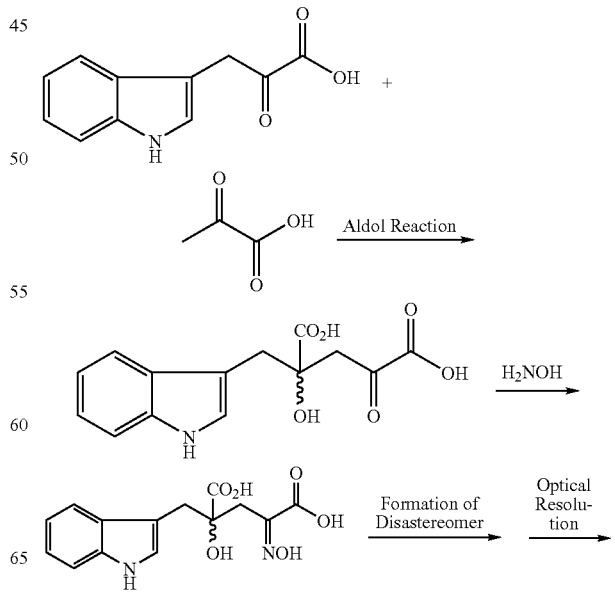

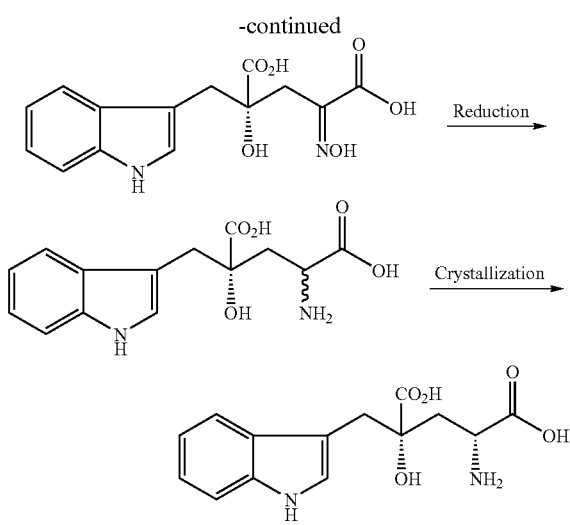

As compared with the conventional processes, the above producing process comprises less steps, is able to produce an optically active monatin in an efficient manner and is a producing process which is suitable in industry as well. However, an optical isomer concerning 2-position which is out of the object is separated to the mother liquor side and, if it is isomerized, for example, to convert to an aimed optically active monatin, the efficiency is further enhanced.

The present applicant has also found and reported that, among the four optical isomers of monatin, monatins where steric configuration at 2-position is R or, in other words, (2R,4R) monatin and (2R,4S) monatin are far better in terms of intensity as a sweetener than monatins where steric configuration at 2-position is S (refer to Patent Document 5: WO 03/045,914) Therefore, it is convenient in using monatin as a sweetener if 2-position of (2S,4S) monatin or (2S,4R) monatin having lower strength of sweetness is isomerized whereby each of them is able to be efficiently induced to (2R,4S) monatin or (2R,4R) monatin, respectively.

With regard to a method for racemization of optically active substance of amino acid or the like, there have been known, for example, a method where treatment is conducted under strongly acidic or strongly alkaline condition or at high temperature and a method where racemization is conducted under a relatively mild condition in the presence of an aldehyde (refer to Patent Document 6: Japanese Patent Laid-Open No. 57/123,150; and Patent Document 7: Japanese Patent Laid-Open No. 58/167,562) but, in those methods, the maximum yield is about 50% since isomerization ratio is converged to 1:1 whereby they are unable to be said to be efficient racemization method. A method of isomerization and separation in which aimed optical isomer is produced in a high yield by combining with a specific optically active substance has been also known (refer to Non-Patent Document 4: *Tetrahedron*, 1997, Vol. 53, No. 28, pages 9417 to 9476; Non-Patent Document 5: *Tetrahedron Asymmetry*, 2002, Vol. 13, pages 2649 to 2652) but enormous trials-and-errors are necessary for finding such a combination.

[Patent Document 1]
  Japanese Patent Laid-Open No. 64/025,757
[Patent Document 2]
  U.S. Pat. No. 5,994,559
[Patent Document 3]
  Japanese Patent Laid-Open No. 2002/060,382
[Patent Document 4]
  WO 03/059,865
[Patent Document 5]
  WO 04/045,914
[Patent Document 6]
  Japanese Patent Laid-Open No. 57/123,150
[Patent Document 7]
  Japanese Patent Laid-Open No. 58/167,562
[Non-Patent Document 1]
  *Tetrahedron Letters,* 2001, Vol. 42, No. 39, pages 6793 to 6796
[Non-Patent Document 2]
  *Organic Letters,* 2000, Vol. 2, No. 19, pages 2967 to 2970
[Non-Patent Document 3]
  *Synthetic Communication,* 1994, Vol. 24, No. 22, pages 3197 to 3211
[Non-Patent Document 4]
  *Tetrahedron,* 1997, Vol. 53, No. 28, pages 9417 to 9476
[Non-Patent Document 5]
  *Tetrahedron Asymmetry,* 2002, Vol. 13, pages 2649 to 2652

DISCLOSURE OF THE INVENTION

Problems that the Invention is to Solve

An object of the invention is to provide a process for producing monatin where steric configuration of 2-position is in an R configuration by isomerization of 2-position of monatin where steric configuration of 2-position is in an S configuration or a salt thereof.

Means for Solving the Problems

In solving the above-mentioned problems, the present inventors have carried out intensive investigations and found that, when isomerization (epimerization) of 2-position of monatin where steric configuration of 2-position is in an S configuration (hereinafter, it will be sometime abbreviated as (2S) monatin) is conducted in a mixed solvent of water and organic solvent and then monatin where steric configuration of 2-position is in an R configuration (hereinafter, it will be sometimes abbreviated as (2R) monatin) or a salt thereof is crystallized, (2R) monatin is able to be predominantly prepared and also found that, when (2S) monatin is removed by crystallization before crystallization of (2R) monatin and then (2R) monatin is crystallized, (2R) monatin having far higher purity is able to be prepared.

Thus, the invention covers the following contents.

[1] A process for producing monatin where steric configuration of 2-position is in an R configuration or a salt thereof, characterized in that, the process contains a step where isomerization reaction of 2-position of monatin in which steric configuration of 2-position is in an S configuration is carried out in a mixed solvent of water and organic solvent in the presence of an aldehyde, a step where the isomerization is carried out and, after that, a step where monatin in which steric configuration of 2-position is in an R configuration or a salt is crystallized.

[2] The process for producing according to the above [1] wherein the step where monatin in which steric configuration of 2-position is in an R configuration or a salt thereof is crystallized which is conducted after the step for conducting an isomerization is carried out in such a manner that monatin in which steric configuration of 2-position is an in an S configuration or a salt thereof is removed by crystallization from the reaction solution and monatin in which steric configuration of 2-position is an in R configuration or a salt thereof is crystallized from the mother liquor for crystallization.

[3] The process for producing according to the above [1], wherein the step where monatin in which steric configuration of 2-position is in an R configuration is crystallized which is carried out after the step where isomerization is conducted is done by means of recrystallization of crystals prepared by crystallization of the reaction solution.

[4] The process for producing according to the above [1] to [3], wherein the isomerization reaction is carried out in the presence of monatin in which steric configuration of 2-position is in an S configuration and monatin in which steric configuration of 2-position is in an R configuration.

[5] The process for producing according to the above [1] to [3], wherein the aldehyde is an aromatic aldehyde.

[6] The process for producing according to the above [5], wherein the aromatic aldehyde is salicylaldehyde.

[7] The process for producing according to the above [1] to [3], wherein the organic solvent is an alcohol.

[8] The process for producing according to the above [1] to [3], wherein it is conducted under the condition in which pH of the reaction solvent for the isomerization is 2 to 8.

[9] The process for producing according to the above [1] to [3], wherein the reaction temperature for the isomerization reaction is 60 to 90° C.

[10] A process for producing (2R,4R) monatin or a salt thereof, characterized in that, the process includes a step where isomerization reaction at 2-position of (2S,4R) monatin represented by the formula (1)

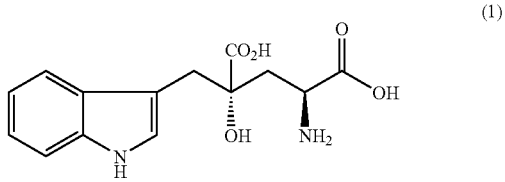

(1)

is carried out and then (2R,4R) monatin represented by the formula (2)

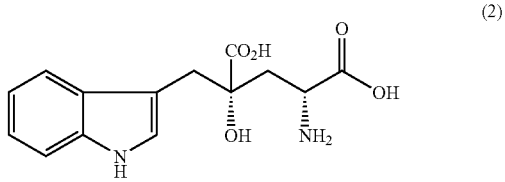

(2)

or a salt thereof is crystallized.

[11] The production process according to [10], wherein the step where (2R,4R) monatin or a salt thereof is crystallized represented by the formula (2) which is conducted after the step where the isomerization is done is carried out by such a manner that (2S,4R) monatin represented by the formula (1) or the salt thereof is removed by crystallization for the reaction solution and then (2R,4R) monatin represented by the formula (2) or the salt thereof is crystallized from the mother liquor after the crystallization.

[12] The production process according to [10], wherein the step where (2R,4R) monatin represented by the formula (2) or a salt thereof is crystallized which is carried out after the step where isomerization reaction is done is conducted by means of recrystallization of crystals prepared by crystallization of the reaction solution.

[13] The process for producing according to the above [10] to [12] wherein the isomerization reaction is carried out in the presence of (2S,4R) monatin represented by the formula (1) and (2R,4R) monatin represented by the formula (2).

[14] The process for producing according to the above [10] to [12], wherein the aldehyde is an aromatic aldehyde.

[15] The process for producing according to the above [14], wherein the aromatic aldehyde is salicylaldehyde.

[16] The process for producing according to the above [10] to [12], wherein the organic solvent is an alcohol.

[17] The process for producing according to the above [10] to [12], wherein it is conducted under the condition in which pH of the reaction solvent for the isomerization is 2 to 8.

[18] The process for producing according to the above [10] to [12], wherein the reaction temperature for the isomerization reaction is 60 to 90° C.

Incidentally, in the invention, monatin in which steric configuration of 2-position is in an S configuration is a term standing for (2S,4R) monatin and/or (2S,4S) monatin while monatin in which steric configuration of 2-position is in an R configuration is a term standing for (2R,4R) monatin and/or (2R,4S) monatin.

BEST MODE FOR CARRYING OUT THE INVENTION

With regard to monatin which is used as a starting material for the producing process of the invention, its examples include not only the case where (2S,4R) monatin or (2S,4S) monatin is present solely but also a mixture where (2S,4R) monatin and (2R,4R) monatin are present in any ratio and a mixture where (2S,4S) monatin an (2R,4S) monatin are present in any ratio.

The producing process according to the invention is able to be used particularly advantageously in the case where (2R, 4R) monatin is aimed to be selectively prepared from monatins where 4-position is optically active in which (2S,4R) monatin and (2R,4R) monatin are present in any ratio or in the case where (2R,4S) monatin is aimed to be selectively prepared from monatins where 4-position is optically active in which (2S,4S) monatin and (2R,4S) monatin are present in any ratio.

The monatin which is used as a starting material for the producing process according to the invention may be in a form of various salts such as sodium salt, potassium salt and ammonium salt. Further, (2R,4R) monatin and (2R,4S) monatin which are prepared by the producing process according to the invention may also be in a form of various salts. Those various kinds of monatin may be produced by the method mentioned, for example, in Patent Document 4 or Patent Document 5.

When the process for producing an optically active monatin mentioned in Patent Document 4 is taken an example, (4R)-4-hydroxy-4-(3-indolylmethyl)-2-hydroxyimino-glutamic acid represented by the formula (4), for example, is subjected to a hydrogenation reaction using a catalyst such as a rhodium carbon to give a reaction mixture containing (2S, 4R) monatin and (2R,4R) monatin. The catalyst in the reaction mixture is filtered and crystallized from a mixed solvent of water and alcohol whereupon (2R,4R) monatin is able to be produced selectively.

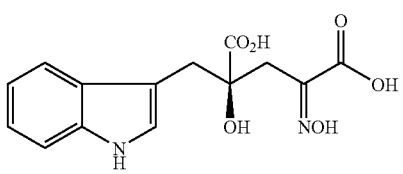

(4)

In that case, (2S,4R) monatin contained in the reaction mixture is selected to the mother liquor side. However, when isomerization is carried out together with crystallization under the specific condition in accordance with the producing process of the invention and (2S,4R) monatin is converted to (2R,4R) monatin, then it is possible to prepare (2R,4R) monatin more efficiently.

Further, as compared with (2R,4R) monatin which is an aimed product, (2S,4R) monatin which is an optical isomer concerning 2-position of the above is contained in a high ratio in a mother liquor of crystallization after preparation of (2R, 4R) monatin from a reaction mixture of (2R,4R) monatin and (2S,4R) monatin by crystallization. It is also possible that the mother liquor is subjected to the producing process according to the invention so that (2S,4R) monatin is isomerized to (2R,4R) monatin whereby (2R,4R) monatin is recovered from the mother liquor. It is more efficient that the isomerization reaction is applied not to the reaction mixture before crystallization where an isomer of the aimed product is contained in a higher ratio but to a crystallized mother liquor where an isomer of the aimed product is contained in a lower ratio so that an equilibrated mixture where (2R,4R) monatin which is an aimed product is abundant. When crystals of (2R,4R) monatin prepared by the process of the invention from the crystallized mother liquor as such are circulated to a step of a series of process for producing monatin, it is possible to enhance the productivity. For example, when the monatin crystals are added to a reaction mixture in a step for crystallization of (2R,4R) monatin from a reaction mixture of (2S, 4R) monatin and (2R,4R) monatin, it is possible to produce (2R,4R) monatin more efficienty. When purity of crystal of (2R,4R) monatin prepared from the crystallized mother liquor is high, then the crystals may be directly mixed with crystals of (2R,4R) monatin prepared by crystallization from the reaction mixture.

Hereinabove, an illustration is done taking the case where (2R,4R) monatin is prepared as an example but that is also entirely the same for the case where (2R,4S) monatin is prepared. In addition, the isomerization reaction according to the invention is also able to be applied, for example, to a mixture of four kinds of optical isomers of monatin, to a mixture of (2S,4R) monatin and (2R,4S) monatin and to a mixture of (2S,4S) monatin and (2R,4R) monatin. In that case, it is also possible that, depending upon the object for example, a mixture of (2S,4S) monatin and (2R,4R) monatin or a mixture of (2S,4R) monatin and (2R,4S) monatin is prepared (refer to Reference Example 3 which will be mentioned later).

In the producing process according to the invention, an aldehyde is used for the isomerization reaction. With regard to the aldehyde, any of aliphatic and aromatic aldehydes may be used.

With regard to the aliphatic aldehyde, a saturated or unsaturated aldehyde having 1 to 7 carbon(s) such as formaldehyde, acetaldehyde, propionaldehyde, n-butyraldehyde, 1-butyraldehyde, n-valeraldehyde, capronaldehyde, n-heptylaldehyde, acrolein and methacrolein may be used.

With regard to the aromatic aldehyde, benzaldehyde, salicylaldehyde, m-hydroxyaldehyde, p-hydroxyaldehyde, o-nitrobenzaldehyde, p-nitrobenzaldehyde, 5-nitrosalicylaldehyde, anisaldehyde, o-vanillin, vanillin, furfural, pyridoxal, etc. may be used.

With regard to the aldehyde, salicylaldehyde, pyridoxal and o-vanillin are particularly preferred.

The aldehyde may be used within a range of 0.01 to 1.0 molar equivalent, more preferably 0.05 to 0.5 molar equivalent and, still more preferably, 0.1 to 0.3 molar equivalent to the monatin existing in the system.

With regard to the reaction solvent for the isomerization reaction in the producing process according to the invention, a mixed solvent of water and organic solvent is used. As to the organic solvent, an organic solvent which is miscible with water is used and an alcohol such as methanol, ethanol, propanol and isopropanol is particularly preferred. As to the organic solvent, two or more different ones may be mixed and used. The ratio of the organic solvent to water is set in terms of (organic solvent):(water) by volume within a range of from 1:0.01 to 1:1 and, more preferably, from 1:0.1 to 1:0.5.

Temperature for the isomerization reaction is set within a range of preferably 50 to 100° C. and, more preferably, 60 to 90° C. pH for the isomerization reaction is set within a range of usually 2 to 8 and, preferably, 3 to 7. Adjustment of the pH may be carried out using an acid and an alkali. There is no particular limitation for the acid used and an organic acid such as acetic acid or an inorganic acid such as hydrochloric acid and sulfuric acid may be used. There is also no particular limitation for the alkali and an alkali metal hydroxide such as sodium hydroxide and potassium hydroxide and an organic base such as ammonia and amine may be used.

Reaction time for the isomerization reaction may be set within a range of usually 1 to 48 hour(s) and, preferably, 1 to 6 hour(s). In the isomerization reaction, a lactamized compound of monatin is produced as a result of side reaction and, since there is a tendency that, the longer the reaction time, the more the produced amount of the lactamized compound, it is preferred that the reaction is finished that, in the isomerization reaction, the ratio of (2R) monatin to (2S) monatin reaches the equilibrated value. When the lactamized compound is heated under an alkaline condition, a lactam ring is hydrolyzed to induce to the original monatin an, if necessary, a hydrolyzing step of the lactam may be carried out.

When the reaction solution is crystallized after finishing the isomerization reaction, (2R) monatin or a salt thereof is able to be prepared as crystals. Although there is no particular limitation for the crystallizing method, a method where a base such as sodium hydroxide, potassium hydroxide or ammonia is added to the reaction solution, then the reaction solution is concentrated or a solvent in the reaction solution is evaporated, the residue is dissolved in an appropriate amount of water and an appropriate amount of ethanol is added thereto whereupon crystals of (2R) monatin salt are crystallized may be listed as one of the preferred examples. Incidentally, in the isomerization reaction, the ratio of (2R) monatin to (2S) monatin reaches an equilibrated value after elapse of predetermined time and, when an isomerization reaction is carried out using (2S,4R) monatin for example, the ratio of (2R,4R) monatin to (2S,4R) monatin in the reaction solution is converged to about 2:1. Accordingly, considerable amount of (2S,4R) monatin salt is contained in the crystals prepared by crystallization of the reaction solution by the above-mentioned method and, therefore, in order to prepare (2R,4R) monatin of higher purity, it is preferred that the resulting crystals are recrystallized. The recrystallization may be carried out using a water-ethanol solvent the same as above. When an appropriate amount of acid is added in the recrystallization, it is possible to prepare monatin in a free form and, if necessary, when recrystallization is carried out by addition of an appropriate amount of base, it is also possible to prepare crystals of monatin salt.

It is also possible to efficiently separate the steric isomers by utilizing the difference in solubility of (2S,4R) monatin and (2R,4R) monatin or of (2R,4S) monatin and (2S,4S) monatin in ethanol. Thus, when crystallization is carried out using ethanol as a poor solvent, there is a tendency that crystals of (2S,4R) monatin are predominantly separated out in spite of the fact that the existing ratio of (2S,4R) monatin is little because solubility of (2S,4R) monatin in ethanol is low as compared with (2R,4R) monatin. Therefore, before crystallization of (2R,4R) monatin (salt), (2S,4R) monatin is firstly crystallized and the resulting crystals are removed. The ratio of (2R,4R) monatin in the resulting crystallized mother liquor is significantly higher than that in the reaction solution immediately after the reaction and, therefore, when it is crystallized once again, it is possible to prepare crystals of (2R,4R) monatin salt having higher purity. In case crystals of (2S,4R) monatin are previously removed by means of crystallization, it is possible to efficiently remove (2S,4R) monatin from the reaction solution when the crystallizing temperature is set at as high as about 70 to 80° C. and the crystals prepared by the crystallization are preferably filtered when they are still at high temperature. In addition, the crystals of (2R,4R) monatin (salt) prepared may be recrystallized the same as above for making the purity higher. The above is also the same in the case of (2R,4S) monatin and (2S,4S) monatin.

(2R) monatin prepared in a form of a salt may also be converted to a free compound from the salt by methods which have been known for persons skilled in the art.

As hereunder, the invention will be illustrated in detail by way of Examples although the invention shall not be limited by the Examples at all. Incidentally, measurement of optical purity in Examples was carried out by means of an HPLC under the following conditions.

With regard to $^1$H-NMR, it was measured by Brucker AVANCE 400 (400 MHz) while, with regard to MS spectrum, it was measured by Thermo Quest TSQ 700. As to a cation exchange resin, Amberlite IR 120B H AG was used.

Analysis of monatin by a high performance liquid chromatography was carried out under the following conditions.

(Analytical Condition 1)
Column: Inertsil ODS-80A, 6×150 mm
Eluant: 12% $CH_3CN$ aq 0.05% TFA
Flow rate: 1.5 ml/min
Detection: UV 210 nm
Column temperature: room temperature (Analytical Condition 2)
Column: Crownpack CR(+) 4×150 mm
Eluant: $HClO_4$ aq (pH 2.0)/$CH_3OH$=90/10
Flow rate: 1.2 ml/min
Detection: UV 210 nm
Column temperature: room temperature

EXAMPLE 1

A mixture of sodium salt of (2R,4R) monatin and sodium salt of (2S,4R) monatin [(2R,4R): (2S,4R)=26:74] (3.152 g, 10 mmol), 244 mg (0.2 equivalent) of salicylaldehyde and 601 mg (1.0 equivalent) of acetic acid were added to 60 ml of 25% aqueous solution of methanol and heated with stirring at 85° C. for 6 hours and, when the reaction solution after finishing the heating was analyzed by an HPLC, the ratio of (2R,4R) monatin to (2S,4R) monatin was 63:27. The reaction solution was concentrated in vacuo, 5 ml of water was added so that the residue was dissolved therein and 50 ml of ethanol was added thereto whereupon crystals were separated out. When the resulting one in a state of slurry was heated as it was at 85° C. for 1 hour, the crystals were once dissolved to give a uniform one and then the crystals were separated out again. The reaction solution was filtered when it was still at high temperature and the crystals separated out therefrom were filtered. The ratio of (2R,4R) monatin to (2S,4R) monatin in the resulting crystals was 15:85. The resulting crystals were dissolved in 5% aqueous ammonia and the solution was concentrated in vacuo followed by adding active carbon thereto. The active carbon was removed by filtration and ethanol was added to the filtrate to crystallize whereupon 773 mg [2.50 mmol, (2R,4R): (2S,4R)=4:96] of ammonium salt of (2S,4R) monatin was prepared.

The crystallized mother liquor prepared by the above filtration was adjusted to weakly alkaline with 5 ml of 2N aqueous solution of sodium hydroxide and the reaction solution was concentrated in vacuo. Water (5 ml) was added to the resulting residue to dissolve, 60 ml of ethanol was added thereto, the mixture was stirred and the resulting crystals were filtered. Ratio of (2R,4R) monatin to (2S,4R) monatin in the resulting crystals was 90:10. The resulting crystals were dissolved in 50 ml of water, cation exchange resin was added thereto so that pH was adjusted to nearly neutral and then the cation exchange resin was removed by filtration. Active carbon was added to the filtrate, the mixture was stirred for a while and then the active carbon was removed by filtration. After the filtrate was concentrated in vacuo, ethanol was added thereto to crystallize whereupon 851 mg [2.48 mmol, (2R,4R): (2S,4R)=88:12] of sodium salt of (2R,4R) monatin with 0.6 molar equivalent of ethanol.

Results of $^1$H-NMR and mass analysis of sodium salt crystals of (2R,4R) monatin with 0.6 molar equivalent of ethanol were as follows.

$^1$H-NMR ($D_2O$) [main peaks] δ: 1.95-2.02 (m, 1H), 2.58-2.62 (m, 1H), 3.01-3.05 (m, 1H), 3.21-3.24 (m, 1H), 3.55-3.58 (m, 1H), 7.07-7.11 (m, 1H), 7.14-7.18 (m, 2H), 7.42-7.44 (d, 1H), 7.66-7.68 (d, 1H).

ESI-MS: 291.49 (M-H)$^-$.

Results of $^1$H-NMR and mass analysis of crystals of ammonium salt of (2S,4R) monatin were as follows.

$^1$H-NMR ($D_2O$) [main peaks] δ: 2.11-2.17 (m, 1H), 2.38-2.43 (m, 1H), 3.16 (s, 2H), 3.90-3.93 (m, 1H), 7.06-7.10 (m, 1H), 7.13-7.17 (m, 2H), 7.41-7.43 (d, 1H), 7.66-7.68 (d, 1H).

ESI-MS: 291.19 (M-H)$^-$.

EXAMPLE 2

A mixture of sodium salt of (2R,4R) monatin and sodium salt of (2S,4R) monatin [(2R,4R): (2S,4R)=26:74] (3.152 g, 10 mmol), 244 mg (0.2 equivalent) of salicylaldehyde and 601 mg (1.0 equivalent) of acetic acid were added to 60 ml of 25% aqueous solution of methanol and heated with stirring at 85° C. for 6 hours (pH upon initiation of the reaction=4.27; pH upon finishing the reaction=4.31). After finishing the reaction, 5 ml of 2N aqueous solution of sodium hydroxide was added to the reaction solution (pH=6.21) followed by heating with stirring at 85° C. for 30 minutes. The reaction solution was concentrated in vacuo, the resulting residue was dissolved in 5 ml of water and 75 ml of ethanol was added thereto so that crystals were separated out. The resulting crystals were once dissolved in water, concentrated in vacuo and the residue was crystallized with 100 ml of a 1:1 mixed solvent of isopropanol and ethanol to give crystals of sodium salt of (2R,4R) monatin [(2R,4R):(2S,4R)=64:36]. The crystals were not dried but directly dissolved in water followed by concentrating in vacuo so that the solvent amount was made about 10 ml. To the solution was added 5 ml of 2N aqueous solution of hydrochloric acid and the resulting crystals of free substance of (2R,4R) monatin (crystal 1) were filtered [(2R,4R):(2S,4R)=84:16]. Crystallized mother liquor for the crystal 1 was crystallized with water-ethanol to give crystal 2 [(2R,4R):(2S,4R)=12:88]. Crystallized mother liquor for the crystal 2 was crystallized with water-ethanol to give crystal 3 [(2R,4R):(2S,4R)=85:15]. The crystals 1 and 3 were combined and dissolved in 5% aqueous ammonia, the reaction solution was concentrated in vacuo and ethanol was added to the residue to crystallize. The crystallizing operation was repeated once again to give crystals of ammonium salt of (2R,4R) monatin in 1.19 g [3.38 mmol; (2R,4R): (2S,4R)=92:8]. Crystallized mother liquors for the crystals 2 and 3 were combined and crystallized from water-ethanol to give ammonium salt of (2S,4R) monatin in 978 mg [3.16 mmol; (2R,4R):(2S,4R)=33:67].

REFERENCE EXAMPLE 1

A 26:74 mixture (158 mg, 0.5 mmol) of sodium salt of a (2R,4R) substance of monatin and sodium salt of a (2S,4R) substance of monatin was dissolved in 3 ml of 50% aqueous solution of methanol and predetermined amounts of acetic acid and salicylaldehyde were added thereto. The reaction solution was heated at 85° C. and the ratio of the (2R,4R) substance of monatin to the (2S,4S) substance of monatin was measured by means of an HPLC. At the same time, lactam of the monatin which was a by-product was measured. Incidentally, most of the produced lactam was a steric isomer derived from monatin of the (2R,4R) substance.

TABLE 1-1

Epimerization Rate [Existing Ratio (%) of (2R, 4R) Substance] Salicylaldehyde (0.2 Equivalent)

| Acetic Acid | Reaction Time | | |
|---|---|---|---|
| (Equivalent(s)) | 1 Hour | 3 Hours | 6 Hours |
| 1.0 | 41.6 | 56.7 | 64.6 |
| 1.5 | 43.1 | 58.8 | 65.8 |
| 2.0 | 45.0 | 59.7 | 66.1 |

TABLE 1-2

Epimerization Rate [Existing Ratio (%) of (2R, 4R) Substance] Salicylaldehyde (0.5 Equivalent)

| Acetic Acid | Reaction Time | | |
|---|---|---|---|
| (Equivalent(s)) | 1 Hour | 3 Hours | 6 Hours |
| 1.0 | 44.9 | 59.2 | 64.7 |
| 1.5 | 47.7 | 61.1 | 65.4 |
| 2.0 | 48.5 | 61.0 | 65.6 |

TABLE 1-3

Epimerization Rate [Existing Ratio (%) of (2R, 4R) Substance] Salicylaldehyde (1.0 Equivalent)

| Acetic Acid | Reaction Time | | |
|---|---|---|---|
| (Equivalent(s)) | 1 Hour | 3 Hours | 6 Hours |
| 1.0 | 47.3 | 59.5 | 63.7 |
| 1.5 | 49.3 | 60.7 | 64.0 |
| 2.0 | 50.9 | 61.0 | 64.1 |

TABLE 2

Producing Rate of Lactam (HPLC Area %)

| Acetic Acid | Reaction Time | | |
|---|---|---|---|
| (Equivalent(s)) | 1 Hour | 3 Hours | 6 Hours |
| 1.0 | 2.7 | 6.3 | 11.6 |
| 1.5 | 2.7 | 7.2 | 13.4 |
| 2.0 | 3.2 | 7.7 | 14.5 |

REFERENCE EXAMPLE 2

A 26:74 mixture (0.5 mmol) of sodium salt of (2R,4R) monatin and sodium salt of (2S,4R) monatin was dissolved in 4 ml of 25%, 50% or 75% aqueous solution of methanol and 1.0 equivalent of acetic acid and 0.2 equivalent of salicylaldehyde were added thereto. The reaction solution was heated at 85° C. and the ratio of a (2R,4R) substance of monatin to a (2S,4S) substance of monatin was measured by means of an HPLC. At the same time, lactam of the monatin which was a by-product was measured. Incidentally, most of the produced lactam was a steric isomer derived from monatin of the (2R, 4R) substance.

TABLE 3

Epimerization Rate [Existing Ratio (%) of (2R, 4R) Substance] Influence of Ratio of Methanol in the Solvent

| Methanol | Reaction Time | | |
|---|---|---|---|
| (%) | 1 Hour | 3 Hours | 6 Hours |
| 25 | 33.9 | 55.3 | 63.5 |
| 50 | 40.9 | 56.6 | 64.1 |
| 75 | 38.3 | 53.2 | 61.8 |

TABLE 4

Producing Rate of Lactam (HPLC Area %)

| Methanol | Reaction Time | | |
|---|---|---|---|
| (%) | 1 Hour | 3 Hours | 6 Hours |
| 25 | 1.8 | 4.2 | 7.7 |
| 50 | 2.6 | 5.7 | 10.7 |
| 75 | 2.4 | 6.6 | 11.9 |

REFERENCE EXAMPLE 3

A mixture of ammonium salt of (2S,4R) monatin and ammonium salt of (2R,4S) monatin [(2S,4R):(2R,4S)=1:1] in an amount of 300 mg (0.97 mmol), 233 mg (4.0 equivalent) of acetic acid and 120 mg (1.0 equivalent) of salicylaldehyde were added to 30 ml of methanol and the reaction solution was stirred at 80° C. for 16 hours. When the reaction solution was analyzed by means of an HPLC, [(2S,4S) substance of monatin]: [(2R,4R) substance and (2R,4S) substance of monatin] was 45:55.

The reaction solution was concentrated in vacuo and 1.5 ml of 2N aqueous solution and 30 ml of water were added to the residue. After the reaction solution was heated at 80° C. for 30 minutes, the reaction solution was neutralized by addition of cation exchange resin thereto. After the resin was removed by filtration, the filtrate was concentrated in vacuo The residue was crystallized using water and ethanol and the crystals were collected by filtration to give 200 mg of a mixture of four kinds of steric isomers of sodium salt of monatin. When the crystals were analyzed by means of an HPLC, they were found to be [(2S,4S) substance of monatin+(2R,4R) substance of monatin]:[(2S,4R) substance of monatin+(2R,4S) substance of monatin]=43:57.

INDUSTRIAL APPLICABILITY

In accordance with the invention, (2S) monatin is able to be induced, by an isomerization reaction, to (2R) monatin which has a higher intensity of sweetness and, particularly, (2R) monatin is easily able to be predominantly prepared in a system in which (2S) monatin and (2R) monatin are mixed whereby the invention is advantageous for the production of (2R,4R) monatin and (2R,4S) monatin in an industrial scale.

The invention claimed is:

1. A process for producing monatin in which the steric configuration at the 2-position is in the R configuration or a salt thereof,
   wherein said process comprises:
   (1) isomerizing the 2-position of monatin in which the steric configuration of 2-position is in the S configuration in a mixed solvent of water and at least one organic solvent in the presence of at least one aldehyde, to obtain monatin in which the steric configuration at the 2-position is in the R configuration;
   (2) and crystallizing said monatin in which the steric configuration at 2-position is in the R configuration or a salt thereof.

2. The process according to claim 1, wherein said crystallizing is carried out in such a manner that monatin in which the steric configuration at the 2-position is in the S configuration or a salt thereof is removed by crystallization from the reaction solution and monatin in which the steric configuration at the 2-position is in the R configuration or a salt thereof is crystallized from the mother liquor used for crystallization.

3. The process according to claim 1, wherein said crystallizing comprises recrystallization of crystals obtained by crystallization from the reaction solution.

4. The process according to claim 1, wherein said isomerizing is carried out in the presence of monatin in which the steric configuration at the 2-position is in the S configuration and monatin in which the steric configuration at the 2-position is in the R configuration.

5. The process according to claim 1, wherein said at least one aldehyde comprises an aromatic aldehyde.

6. The process according to claim 5, wherein said aromatic aldehyde comprises salicylaldehyde.

7. The process according to claim 1, wherein said at least one organic solvent comprises an alcohol.

8. The process according to claim 1, wherein said isomerizing is conducted under a condition in which the pH of said solvent is 2 to 8.

9. The process according to claim 1, wherein said isomerizing is carried out at a temperature of 60 to 90° C.

10. A process for producing (2R,4R) monatin or a salt thereof,
    wherein said process comprises:
    (1) isomerizing the 2-position of (2S,4R) monatin represented by formula (1):

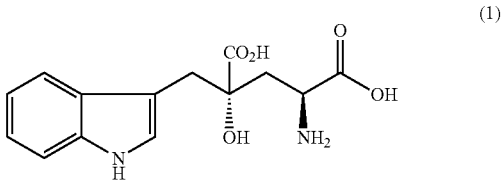

to obtain (2R,4R) monatin represented by formula (2):

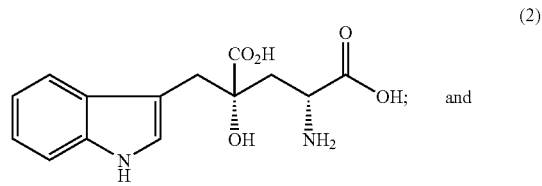

(2) crystallizing said (2R,4R) monatin or a salt thereof.

11. The process according to claim 10, wherein said crystallizing is carried out in such a manner that (2S,4R) monatin represented by formula (1) or a salt thereof is removed by crystallization from the reaction solution and then (2R,4R) monatin represented by formula (2) or a salt thereof is crystallized from the mother liquor after the crystallization.

12. The process according to claim 10, wherein said crystallizing comprises recrystallization of crystals prepared by crystallization from the reaction solution.

13. The process according to claim 10, wherein said isomerizing is carried out in the presence of (2S,4R) monatin represented by formula (1) and (2R,4R) monatin represented by formula (2).

14. The process according to claim 10, wherein said isomerizing is conducted in the presence of at least one aldehyde.

15. The process according to claim 10, wherein said at least one aldehyde comprises an aromatic aldehyde.

16. The process according to claim 15, wherein said aromatic aldehyde comprises salicylaldehyde.

17. The process according to claim 10, wherein said isomerizing is conducted in a mixed solvent of water and at least one organic solvent.

18. The process according to claim 17, wherein said at least one organic solvent comprises an alcohol.

19. The process according to claim 17, wherein said isomerizing is conducted under a condition in which the pH of said solvent is 2 to 8.

20. The process according to claim 10, wherein said isomerizing is carried out at a temperature of 60 to 90° C.

* * * * *